(12) United States Patent
Reif et al.

(10) Patent No.: US 9,045,722 B2
(45) Date of Patent: Jun. 2, 2015

(54) MIXING SYSTEM

(75) Inventors: Oscar-Werner Reif, Hanover (DE);
Gerhard Greller, Goettingen (DE);
Juergen Van Den Boogaard, Dransfeld (DE); Sven Luehmann, Northeim (DE);
Marco Lohrengel, Hattorf am Harz (DE)

(73) Assignee: Sartorius Stedim Biotech GmbH (DE)

( * ) Notice: Subject to any disclaimer, the term of this patent is extended or adjusted under 35 U.S.C. 154(b) by 1129 days.

(21) Appl. No.: 12/991,461

(22) PCT Filed: May 7, 2009

(86) PCT No.: PCT/EP2009/003254
§ 371 (c)(1),
(2), (4) Date: Nov. 8, 2010

(87) PCT Pub. No.: WO2009/143956
PCT Pub. Date: Dec. 3, 2009

(65) Prior Publication Data
US 2011/0058447 A1    Mar. 10, 2011

(30) Foreign Application Priority Data

May 28, 2008    (DE) .......................... 10 2008 025 508

(51) Int. Cl.
*B01F 7/16*    (2006.01)
*B01F 13/02*    (2006.01)
(Continued)

(52) U.S. Cl.
CPC .............. *C12M 23/14* (2013.01); *B01F 7/1695* (2013.01); *B01F 13/0827* (2013.01);
(Continued)

(58) Field of Classification Search
CPC .. B01F 13/08; B01F 13/0827; B01F 13/0836; B01F 13/0845; B01F 13/0854; B01F 13/0863; B01F 13/089
USPC .................................................... 366/273, 274
See application file for complete search history.

(56) References Cited

U.S. PATENT DOCUMENTS 5,368,390 A * 11/1994 Gambrill et al. .............. 366/273
(Continued)

FOREIGN PATENT DOCUMENTS

| DE | 10 2006 022 651 | 10/2007 |
| JP | 2006-212542 | 8/2006 |
| WO | WO 2011/020474 | * 2/2011 |

OTHER PUBLICATIONS

International Preliminary Report on Patentability, of PCT/EP2009/003254, PCT/ISA/237, report dated Dec. 6, 2010, 8 pages.

*Primary Examiner* — Tony G Soohoo
(74) *Attorney, Agent, or Firm* — Gerald E. Hespos; Michael J. Porco; Matthew T. Hespos

(57) ABSTRACT

A mixing system has a container with flexible walls (1), a fluid-tight drive space (6) and a mixing device. The container with flexible walls (1) has at least one head plate (5). The fluid-tight drive space (6) is outside of the container interior (2), and is enclosed by the head plate (5) and a cap (7) attached to the head plate (5). The mixing device has a stirrer shaft (3), onto which stirrer elements (4, 4') are attached. The stirrer shaft (3) is guided from the container interior (2) through an opening in the head plate (5) and the section of the stirrer shaft (3) in the drive space (6) is guided by bearings (9, 10). A seal (8) is fit into the opening of the head plate, and encloses the stirrer shaft (3) and seals the container interior (2) from the drive space (6).

6 Claims, 1 Drawing Sheet

(51) Int. Cl.
*B01F 15/00* (2006.01)
*C12M 1/00* (2006.01)
*B01F 13/08* (2006.01)
*C12M 1/06* (2006.01)

(52) U.S. Cl.
CPC .... *B01F 15/00071* (2013.01); *B01F 15/00831* (2013.01); *B01F 15/0085* (2013.01); *B01F 2015/00084* (2013.01); *B01F 2215/0032* (2013.01); *B01F 2215/0073* (2013.01); *C12M 27/02* (2013.01)

(56) References Cited

U.S. PATENT DOCUMENTS

| | | | |
|---|---|---|---|
| 7,547,135 B2* | 6/2009 | Kocienski | 366/273 |
| 2005/0239199 A1* | 10/2005 | Kunas et al. | 435/297.1 |
| 2006/0280028 A1* | 12/2006 | West et al. | 366/331 |
| 2007/0053238 A1* | 3/2007 | Kocienski | 366/273 |
| 2008/0025144 A1* | 1/2008 | Kocienski et al. | 366/270 |

* cited by examiner

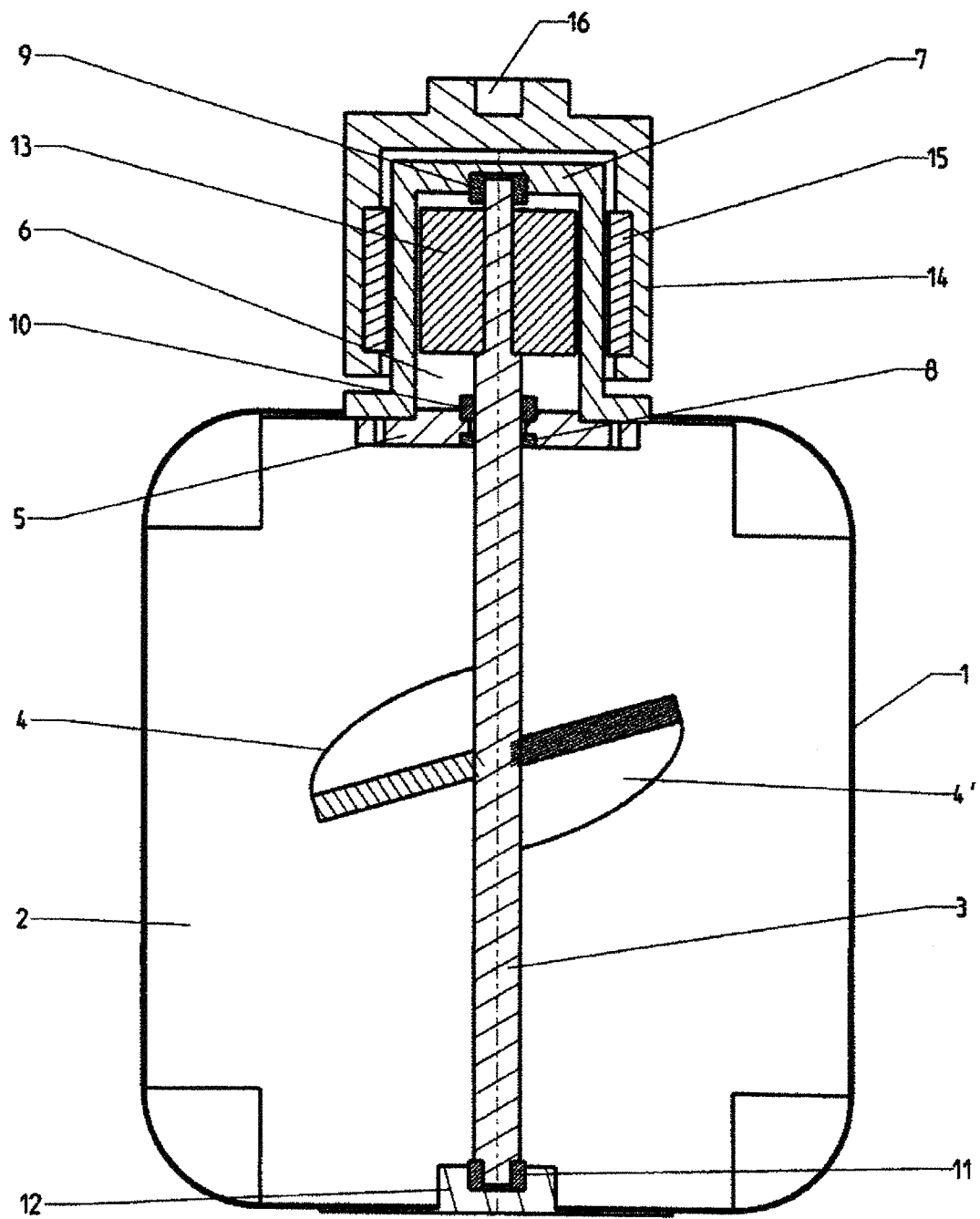

MIXING SYSTEM

BACKGROUND OF THE INVENTION

1. Field of the Invention

The invention relates to a mixing system for a container with flexible walls.

2. Description of the Related Art

Single-use containers with flexible walls are increasingly used in biotechnology and in the pharmaceutical industry for mixing liquids, dissolving solids in liquids or cultivating cells and microorganisms. Here, an advantage of single-use containers made of plastic is that they can already be supplied by the supplier in a clean and, where necessary, sterile state, as a result of which complex cleaning procedures and validations pre-use are dispensed with.

Rotating stirrer shafts provided with stirrer elements such as e.g. propellers are particularly suitable for effectively mixing media in single-use containers with flexible walls. In order to drive such stirrer shafts, it has proven its worth to couple the torque from the motor onto the stirrer shaft by a contactless magnetic coupling, which can be operated without wear-and-tear.

U.S. Patent Application Publication No. 2007/0053238 A1 describes a magnetic coupling for a stirrer shaft in which the drive components, such as bearings and magnets, are situated outside of the container interior. However, a disadvantage of this embodiment is that the container interior, which contains the media to be mixed, is not sealed from the drive components. Thus, the first bearing for accommodating the stirrer shaft is located directly at the opening between the container interior and the magnetic coupling. As a result of this arrangement, bearings and the magnets (drive magnets) affixed to the stirrer shaft can come into contact with the media to be mixed and can be damaged by corrosion. Conversely, it is possible for particles originating from the bearings or the magnets to reach the container interior and thus lead to a contamination of the mixture. This is all the more serious because these mechanical components are generally made of metals and can therefore not be sterilized without problems by gamma radiation.

The object of the invention therefore consists of proposing a cost-effective mixing system with a drive for a single-use container, in which the sterility of the container interior is ensured.

SUMMARY OF THE INVENTION

According to the invention, the object is achieved by a mixing system comprising a container with flexible walls and at least one head plate. A fluid-tight drive space is situated outside of the container interior. The drive space is enclosed by the head plate and a cap attached to the head plate. A mixing device has a stirrer shaft made of plastic, onto which stirrer elements made of plastic are attached. The stirrer shaft is guided from the container interior through an opening in the head plate. The section of the stirrer shaft situated in the drive space is guided by one or more bearings, and a seal is fitted into the opening of the head plate. The seal encloses the stirrer shaft and seals the container interior from the drive space.

In a particular embodiment, the mixing system has drive magnets on the section of the stirrer shaft situated in the drive space. The drive magnets are coupled by magnetic forces to rotor magnets of a rotor, which is situated outside of the drive space. A rotation of the rotor can be brought about by a motor and can be transmitted to the stirrer shaft. In a further embodiment, the stirrer shaft is driven by a motor situated in the drive space. The motor is designed to be disposable as a disposable motor in a preferred embodiment of the invention.

In addition to the bearings on the drive side, the stirrer shaft can be accommodated at the opposite end by a bearing in a base plate of the container. At least one of the aforementioned bearings can be a plain bearing. The bearings can be made completely of plastic.

In a further embodiment, the aforementioned cap can be disassembled and the stirrer shaft is embodied such that it can be divided in the region of the drive space. As a result the section of the stirrer shaft can be removed with the drive magnets or with the motor and can be reused or disposed of separately.

The aforementioned seal can be made of polymer materials and can be integrated into the mixing system as a disposable article. The seal can be designed such that it seals the flexible container with respect to gasses, liquids and contaminants.

The invention will be explained in more detail by means of the FIGURE.

BRIEF DESCRIPTION OF THE DRAWING

The FIGURE is a longitudinal cross section of a container in accordance with the invention.

DETAILED DESCRIPTION OF THE PREFERRED EMBODIMENTS

According to the FIGURE, the container 1 encloses a container interior 2 used to accommodate a liquid. In the container interior 2 there is a mixing device consisting of a stirrer shaft 3 made of plastic and stirring elements 4 and 4' made of plastic. The stirrer shaft 3 penetrates the container 1 in the region of a head plate 5 and ends in a drive space 6, which is enclosed by a cap 7. A seal 8 is embedded in the head plate 5 and surrounds the stirrer shaft 3 and separates the container interior 2 from the drive space 6 and seals these against the passage of fluids or particles. The stirrer shaft 3 is accommodated by a first plain bearing 9 at its upper end, the latter being connected to the cap 7. Moreover, the stirrer shaft 3 is borne by a second plain bearing 10 that is fitted into the head plate 5. A third plain bearing 11, fitted into a base plate 12, accommodates the stirrer shaft 3 at the lower end. The torque for driving the stirrer shaft 3 is taken up via drive magnets 13, which are situated in the drive space 6 and are attached to the upper end of the stirrer shaft 3. A rotor 14 is put over the cap 7, with the rotor magnets 15 being affixed to the rotor 14. The rotor 14 is connected to a motor via a motor connector 16. If the rotor 14 is made to rotate by the motor, a torque is transmitted from the rotor magnets 15 to the drive magnets 13, which in turn set into motion the stirrer shaft 3 with the stirrer elements 4 and 4'.

The invention claimed is:

1. A mixing system comprising:
   a container with flexible walls (1) with at least one head plate (5),
   a cap (7) attached to the head plate (5) and being configured so that a fluid-tight drive space (6) is defined between the cap (7) and the head plate (5) at a position outside of the container interior (2),
   a mixing device with a stirrer shaft (3) made of plastic, onto which stirrer elements (4, 4') made of plastic are attached, the stirrer shaft (3) being guided from the container interior (2) through an opening in the head plate (5), a section of the stirrer shaft (3) situated in the drive space (6) being guided by one or more bearings (9, 10), a seal (8) being fitted into the opening of the head plate, the seal enclosing the stirrer shaft (3) and sealing the container interior (2) from the drive space (6), drive magnets (13) attached to a section of the stirrer shaft (3) situated in the drive space (6), the drive magnets (13) being coupled by magnetic forces to rotor magnets (15) of a rotor (14) outside of the drive space (6), the rotor (14) being rotatable by a motor disposed outside the drive space (6) and rotation of the rotor (14) being transmitted to the stirrer shaft (3), the cap (7) being separable from the head plate (5) and the stirrer shaft (3) having a defined separation location in the drive space (6) between the drive magnets (13) and the head plate (5) so that the cap (7) and a section of the stirrer shaft (3) to which the drive magnets (13) are attached can be separated from a remainder of the mixing system and reused or disposed of separately.

2. The mixing system of claim 1, wherein, in addition to the bearings (9, 10) on the drive space (6), the stirrer shaft (3) is accommodated at an opposite end by a bearing (11) in a base plate (12) of the container (1).

3. The mixing system of claim 2, wherein at least one of the bearings (9, 10, 11) is a plain bearing.

4. The mixing system of claim 3, wherein the bearings (9, 10, 11) are made completely of plastic.

5. The mixing system of claim 1, wherein the seal (8) is made of polymer materials and integrated into the mixing system as a disposable article.

6. The mixing system of claim 1, wherein the seal (8) is formed from a material that seals the container (1) with respect to gasses, liquids and contaminants.

* * * * *